US012584536B2

(12) United States Patent
Bouvier et al.

(10) Patent No.: US 12,584,536 B2
(45) Date of Patent: Mar. 24, 2026

(54) ANTI-VIBRATION DAMPING SYSTEM FOR A CARBON FIBER C-ARM MOUNTED ON A MOBILE BASE

(71) Applicant: GE Precision Healthcare LLC, Waukesha, WI (US)

(72) Inventors: Bernard Bouvier, Eragny (FR); Carlos Martinez Ferreira, Paris (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 273 days.

(21) Appl. No.: 18/483,708

(22) Filed: Oct. 10, 2023

(65) Prior Publication Data

US 2025/0116313 A1 Apr. 10, 2025

(51) Int. Cl.
| | |
|---|---|
| *F16F 15/08* | (2006.01) |
| *A61B 6/00* | (2024.01) |
| *B60B 33/04* | (2006.01) |

(52) U.S. Cl.
CPC ............ *F16F 15/08* (2013.01); *A61B 6/4405* (2013.01); *A61B 6/4441* (2013.01); *B60B 33/045* (2013.01); *B60B 2200/26* (2013.01); *B60B 2900/131* (2013.01)

(58) Field of Classification Search
CPC .............................. A61B 6/4405; A61B 6/4441
See application file for complete search history.

(56) References Cited

U.S. PATENT DOCUMENTS

| | | | | |
|---|---|---|---|---|
| 10,517,553 | B2 * | 12/2019 | Barker ................. | A61B 6/4441 |
| 11,457,883 | B1 * | 10/2022 | Hartley ................. | A61B 6/032 |

| | | | | |
|---|---|---|---|---|
| 2008/0170669 | A1 * | 7/2008 | Jensen ................. | A61B 6/4405 378/197 |
| 2010/0195949 | A1 * | 8/2010 | Yagi ..................... | A61B 6/4441 384/535 |
| 2012/0106701 | A1 * | 5/2012 | Meek ....................... | H05G 1/02 474/84 |
| 2013/0010925 | A1 * | 1/2013 | Martinez Ferreira ....................... | A61B 6/4441 378/62 |
| 2014/0044241 | A1 * | 2/2014 | Furst .................... | A61B 6/4405 378/193 |
| 2015/0335387 | A1 * | 11/2015 | Atzinger .............. | A61B 6/4441 606/130 |
| 2016/0193731 | A1 * | 7/2016 | Sattler .................... | A61B 34/30 901/9 |

(Continued)

*Primary Examiner* — David J Makiya
*Assistant Examiner* — Soorena Kefayati
(74) *Attorney, Agent, or Firm* — Fletcher Yoder, P.C.

(57) ABSTRACT

A mobile X-ray imaging system includes an X-ray radiation source. The mobile X-ray imaging system also includes an X-ray detector. The mobile X-ray imaging system further includes a C-arm having the X-ray radiation source disposed on a first end and the X-ray detector disposed on a second end opposite the first end. The mobile X-ray imaging system further includes a C-arm rotation device coupled to the C-arm and configured to rotate the C-arm in an orbital direction relative to the C-arm rotation device. The mobile X-ray imaging system further includes a mobile base coupled to the C-arm rotation device, wherein the mobile base is configured to move the mobile X-ray imaging system, and wherein the mobile base includes a damping system configured to dampen vibrations that occur when the C-arm deaccelerates to a stop during rotational movement of the C-arm in a single or combined direction.

16 Claims, 11 Drawing Sheets

(56) References Cited

U.S. PATENT DOCUMENTS

| | | | |
|---|---|---|---|
| 2016/0278732 A1* | 9/2016 | Amiri .................... | A61B 6/547 |
| 2017/0000675 A1* | 1/2017 | Hight ................... | A61B 6/0407 |
| 2018/0298970 A1* | 10/2018 | Daugirdas ........... | A61B 6/4476 |
| 2020/0163634 A1* | 5/2020 | Turner ................. | A61B 6/4441 |
| 2021/0145379 A1* | 5/2021 | Simmons .............. | F16F 15/085 |
| 2021/0145383 A1* | 5/2021 | Barker ................. | A61B 6/4441 |

* cited by examiner

ANTI-VIBRATION DAMPING SYSTEM FOR A CARBON FIBER C-ARM MOUNTED ON A MOBILE BASE

BACKGROUND

The subject matter disclosed herein relates to X-ray imaging systems and, more particularly, to a damping system (e.g., anti-vibration damping system) for a mobile X-ray imaging system having a C-arm.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector. During the deceleration phase of the C-arc motion (especially when system is used in manual motion mode (i.e., joystick mode) and due to regulations) of the C-arm, a lot of vibrations are generated for several seconds that may impact image quality (e.g., causing blurriness).

SUMMARY

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with an embodiment, a mobile X-ray imaging system is provided. The mobile X-ray imaging includes an X-ray radiation source. The mobile X-ray imaging system also includes an X-ray detector. The mobile X-ray imaging system further includes a C-arm having the X-ray radiation source disposed on a first end and the X-ray detector disposed on a second end opposite the first end. The mobile X-ray imaging system even further includes a C-arm rotation device coupled to the C-arm and configured to rotate the C-arm relative in an orbital direction relative to the C-arm rotation device. The mobile X-ray imaging system yet further includes a mobile base coupled to the C-arm rotation device via a pivot point configured to rotate both the C-arm rotation device and the C-arm relative to the mobile base, wherein the mobile base is configured to move the mobile X-ray imaging system. The mobile base includes a damping system configured to dampen vibrations that occur when the C-arm deaccelerates to a stop during rotational movement of the C-arm in a single or combined direction.

In accordance with another embodiment, a damping system for a mobile X-ray imaging system is provided. The damping system includes a first plate. The damping system also includes a second plate. The damping system further includes a first damper including at least one elastomeric body disposed between the first plate and the second plate. The mobile X-ray imaging system includes a C-arm made of carbon fiber and having an X-ray radiation source disposed on a first end and an X-ray detector disposed on a second end opposite the first end, a C-arm rotation device coupled to the C-arm and configured to rotate the C-arm in an orbital direction relative to the C-arm rotation device, and a mobile base coupled to the C-arm rotation device via a pivot point configured to rotate both the C-arm rotation device and the C-arm relative to the mobile base, wherein the mobile base is configured to move the mobile X-ray imaging system. The damping system is configured to dampen vibrations that occur when the C-arm deaccelerates to a stop during rotational movement of the C-arm in a single or combined direction.

In accordance with a further embodiment, a mobile base for an X-ray imaging system is provided. The mobile base includes a chassis including a Y-arm, wherein the Y-arm includes a central arm and two arm angled relative to a longitudinal axis of the central arm. The mobile base also includes a first set of wheels. The mobile base further includes a second set of wheels, wherein the first set of wheels and the second set of wheels are coupled to respective ends of the two arms distal from the central arm. The mobile base further includes a damping system including a first set of elastomeric bodies disposed between the first set of wheels and the Y-arm, and a second set of elastomeric bodies disposed between the second set of wheels and the Y-arm. The X-ray imaging system includes a C-arm made of carbon fiber and having an X-ray radiation source disposed on a first end and an X-ray detector disposed on a second end opposite the first end, a C-arm rotation device coupled to the C-arm and configured to rotate the C-arm in an orbital direction relative to the C-arm rotation device, and the C-arm rotation device is coupled to the mobile base via a pivot point configured to rotate both the C-arm rotation device and the C-arm relative to the mobile base. The mobile base is configured to move the X-ray imaging system. The damping system is configured to dampen vibrations that occur when the C-arm deaccelerates to a stop during rotational movement of the C-arm in a single or combined direction.

BRIEF DESCRIPTION OF THE DRAWINGS

These and other features, aspects, and advantages of the present disclosed subject matter will become better understood when the following detailed description is read with reference to the accompanying drawings in which like characters represent like parts throughout the drawings, wherein.

DETAILED DESCRIPTION

Figure 1:
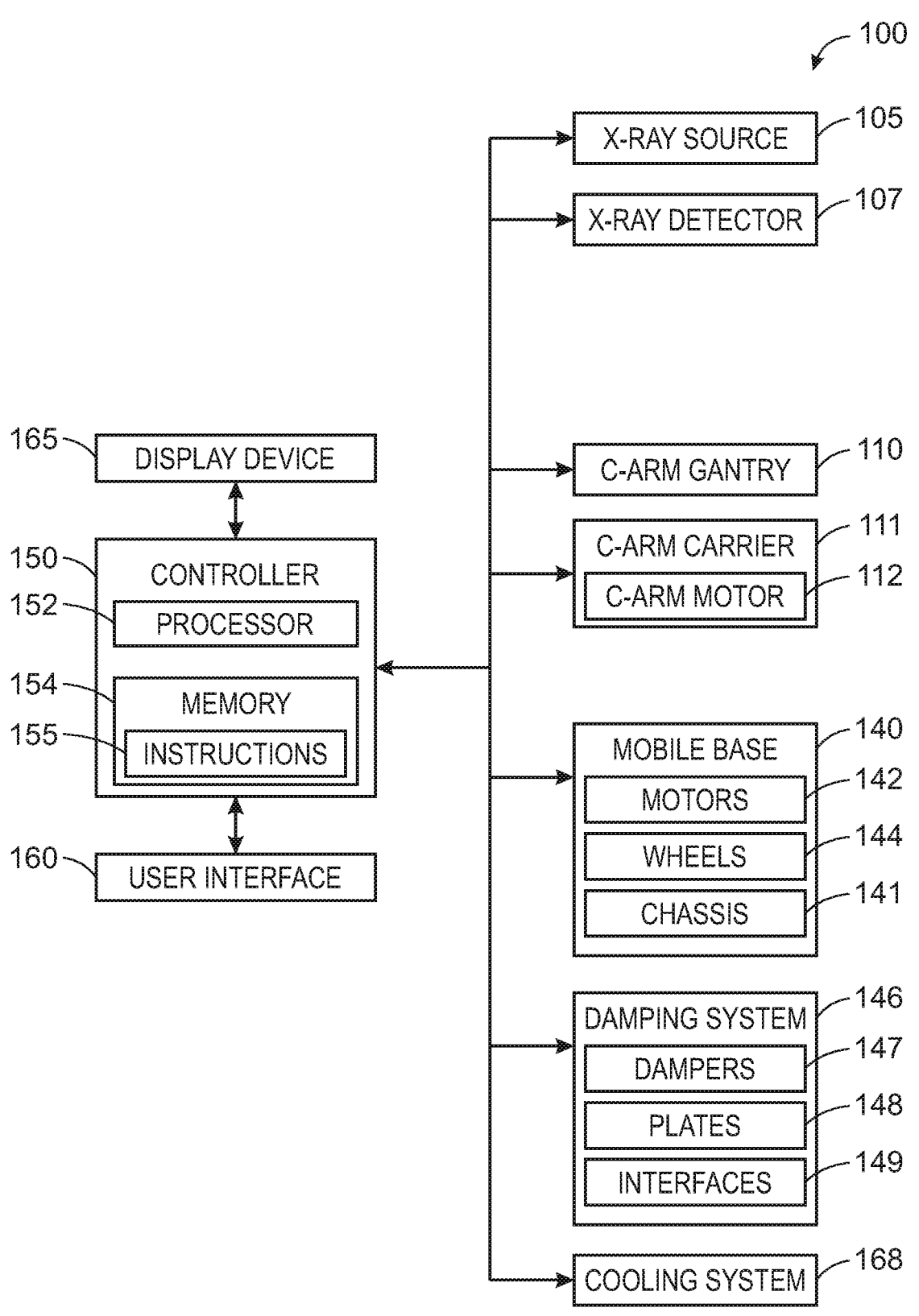
FIG. 1 is a block diagram illustrating components of an example mobile X-ray imaging system, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following embodiments describe an X-ray imaging system (e.g., mobile X-ray imaging system) including an X-ray radiation source. The mobile X-ray imaging system also includes an X-ray detector. The mobile X-ray imaging system further includes a C-arm having the X-ray radiation source disposed on a first end and the X-ray detector disposed on a second end opposite the first end. The mobile X-ray imaging system even further includes a C-arm rotation device coupled to the C-arm and configured to rotate the C-arm in an orbital direction relative to the C-arm rotation device. The mobile X-ray imaging system yet further includes a mobile base (e.g., automated guided vehicle) coupled to the C-arm rotation device, wherein the mobile base is configured to move the mobile X-ray imaging system. The mobile base includes a damping system configured to dampen vibrations that occur when the C-arm deaccelerates to a stop during rotational movement of the C-arm.

In certain embodiments, the C-arm is made of carbon fiber. In certain embodiments, the damping system is configured to dampen vibrations at a frequency of approximately 3 hertz (Hz). In certain embodiments, the mobile base includes a chassis and at least one set of wheels coupled to the chassis, and the damping system includes a damper disposed between the at least one set of wheels (e.g., front wheels) and chassis. In certain embodiments, the chassis includes a Y-arm having a central arm and two arms angled relative to a longitudinal axis of the central arm. The mobile base includes both a first set of wheels (e.g., front wheels) and a second set of wheels (e.g., front wheels) coupled to the chassis at respective ends of the two arms distal from the central arm. The damping system includes both a first damper disposed between the first set of wheels and the chassis and a second damper disposed between the second set of wheels and the chassis.

In certain embodiments, the damper includes at least one elastomeric body. In certain embodiments, the damper includes three elastomeric bodies. In certain embodiments, the damping system includes a first plate, a second plate, and the at least one elastomeric body disposed between the first plate and the second plate. In certain embodiments, the damping system includes an interface having a ball joint (e.g., configured to compensate a defect in floor flatness) coupled to the first plate on a first side of the first plate opposite the at least one elastomeric body. The interface couples the damping system to the chassis. The ball joint is configured to rotate independently of the at least one set of wheels. Also, the ball joint is configured to enable the damping system to tilt laterally relative to a vertical axis. In certain embodiments, the at least one set of wheels are coupled to a second side of the second plate opposite the at least one elastomeric body.

The following embodiments also describe a damping system for a mobile X-ray imaging system. The damping system includes a first plate. The damping system also includes a second plate. The damping system further includes a first damper including at least one elastomeric body disposed between the first plate and the second plate. The mobile X-ray imaging system includes a C-arm made of carbon fiber and having an X-ray radiation source disposed on a first end and an X-ray detector disposed on a second end opposite the first end, a C-arm rotation device coupled to the C-arm and configured to rotate the C-arm in an orbital direction relative to the C-arm rotation device, and a mobile base coupled to the C-arm rotation device and configured to move the mobile X-ray imaging system. The damping system is configured to dampen vibrations that occur when the C-arm deaccelerates to a stop during rotational movement of the C-arm in a single or combined direction (e.g., in a circumferential direction 184 about rotational axis 182 and/or in the orbital direction 174 (see FIG. 2)).

In certain embodiments, the damping system is configured to dampen vibrations at a frequency of approximately 3 Hz. In certain embodiments, the first damper includes three elastomeric bodies. In certain embodiments, the damping system further includes a third plate, a fourth plate, and a second damper including an additional three elastomeric bodies disposed between the third plate and the fourth plate. In certain embodiments, the second late is configured to couple to a first set of wheels (e.g., front wheels) and the fourth plate is configured to couple to a second set of wheels (e.g., front wheels).

In certain embodiments, the damping system further includes a first interface having a first ball joint coupled to the first plate on a first side of the first plate opposite the three elastomeric bodies, and a second interface having a second ball joint coupled to third plate on a second side of the third plate opposite the additional three elastomeric bodies. The first interface and the second interface are both configured to couple the damping system to a chassis of the mobile base. In certain embodiments, the first ball joint is configured to rotate independently of the first set of wheels and the second ball joint is configured to rotate independently of the second set of wheels. In certain embodiments, the first ball joint is configured to enable the first plate, and the second plate, and the three elastomeric bodies to tilt laterally relative to a vertical axis (and to rotate about the vertical axis to add an additional degree of freedom to help with motion control), and the second ball joint is configured to enable the third plate, the fourth plate, and the additional three elastomeric bodies to tilt laterally relative to the vertical axis.

In certain embodiments, the second plate is configured to couple to the first set of wheels on a third side of the second plate opposite the three elastomeric bodies, and the fourth plate is configured to couple the second set of wheels on a fourth side of the fourth plate opposite the additional three elastomeric bodies. In certain embodiments, the chassis includes a Y-arm having a central arm and two arms angled relative to a longitudinal axis of the central arm. The first interface, the first plate, the second plate, and the three elastomeric bodies are all configured to couple at a first end of a first arm of the two arms distal form the central arm. The second interface, the third plate, the fourth plate, and the additional three elastomeric bodies are all configured to couple at a second end of a second arm of the two arms distal from the central arm.

The following embodiments further describe a mobile base for an X-ray imaging system. The mobile base includes a chassis including a Y-arm, wherein the Y-arm includes a central arm and two arm angled relative to a longitudinal axis of the central arm. The mobile base also includes a first set of wheels. The mobile base further includes a second set of wheels, wherein the first set of wheels and the second set of wheels are coupled to respective ends of the two arms distal from the central arm. The mobile base further includes a damping system including a first set of elastomeric bodies disposed between the first set of wheels and the Y-arm, and a second set of elastomeric bodies disposed between the second set of wheels and the Y-arm. The X-ray imaging system includes a C-arm made of carbon fiber and having an X-ray radiation source disposed on a first end and an X-ray detector disposed on a second end opposite the first end, a C-arm rotation device coupled to the C-arm and configured to rotate the C-arm in an orbital direction relative to the C-arm rotation device, and the C-arm rotation device is coupled to the mobile base. The mobile base is configured to move the X-ray imaging system. The damping system is configured to dampen vibrations that occur when the C-arm deaccelerates to a stop during rotational movement of the C-arm in a single or combined direction (e.g., in a circumferential direction 184 about rotational axis 182 and/or in the orbital direction 174 (see FIG. 2)).

The disclosed damping system when located (e.g., vertically located) between the Y-arm of the chassis and the front wheels coupled to the Y-arm enables the absorption of oscillations (e.g., vertical oscillations) or vibrations during the deceleration phase of C-arm motion as it approaches a stop. In particular, the damping system enables the utilization of a C-arm made of carbon fiber (which has a very low damping coefficient relative to aluminum) as part of an interventional C-arm medical imaging system that is configured for manual motion and decelerate with similar timing compared to a C-arm medical imaging system made having a C-arm made aluminum. The damping of the vibrations when the C-arm deaccelerates to a stop during movement of the C-arm in a single or combined direction enables quality images (e.g., lacking blurriness).

FIG. 1 is a block diagram illustrating components of an example mobile X-ray imaging system 100. The mobile X-ray imaging system 100 includes an X-ray source 105 and an X-ray detector 107 mounted on a C-arm gantry 110 (e.g., C-arm). The C-arm gantry 110 may be made of carbon fiber.

The C-arm gantry 110 includes a C-arm motor 112 for adjusting the position of the C-arm gantry 110. More specifically, the C-arm gantry 110 is mechanically coupled to a C-arm carrier 111 (e.g., C-arm rotation device) which includes the C-arm motor 112, and the C-arm motor 112 may be driven to adjust the position of the C-arm gantry 110 with respect to the C-arm carrier 111. For example, the C-arm carrier 111 in conjunction with the C-arm motor 112 is configure to rotate the C-arm gantry 110 in an orbital direction relative to the C-arm carrier 111. In certain embodiments, the C-arm carrier 111 (via a motorized system) is configured to rotate a pivot (e.g., pivot point) where the C-arm carrier 111 is coupled to a mobile base 140 (e.g. automated guided vehicle) or an end of an L-arm coupled to the mobile base 140. The C-arm carrier 111 rotates about a rotational axis (e.g., horizontal axis) of the pivot. In certain embodiments having an L-arm, L-arm may rotate about a location where the other of the L-arm (i.e., the end of the L-arm not connected to the pivot) is coupled to the mobile base 140.

The mobile X-ray imaging system 100 also includes the mobile base 140. The C-arm carrier 111 is coupled to the mobile base 140. The mobile base 140 is configured to move (e.g., translocate) the mobile X-ray imaging system 100 from one location to another location on a floor. The mobile base 140 includes a chassis 141. In certain embodiments, the chassis 141 includes a Y-arm having a central arm and two arms angled relative to a longitudinal axis of the central arm forming a Y-shape. Distal ends of the two arms (i.e., the ends of the two arms located away from the split from the central arm) are located towards a front of the mobile X-ray imaging system 100 (i.e., on the side of the mobile x-ray imaging system 100 with the C-arm gantry 110). The mobile base 140 includes one or more motors 142 for driving one or more wheels 144 (e.g. drive wheels) to adjust a position of the mobile base 140. In addition, one or more of the wheels 144 may be free or un-motorized, as described further herein. For example, the wheels 144 may include a first set of free wheels (e.g., first set of front wheels) and a second set of free wheels (e.g., second set of front wheels). The first set of free wheels and the second set of free wheels may be located on respective ends of the two arms of the Y-arm distal from the central arm.

The mobile X-ray imaging system 100 further includes a damping system 146. The damping system 146 is configured to dampen vibrations that occur when the C-arm gantry 110 (e.g., made of carbon fiber) deaccelerates (e.g., during the deacceleration phase) to a stop during rotational movement of the C-arm gantry 110 in the orbital direction. In certain embodiments, the damping system 146 is configured to dampen vibrations (e.g., oscillations) at a frequency of approximately 3 Hz. The damping system 146 includes dampers 147. For example, respective dampers 147 may be disposed between the first set of front wheels and the chassis 141 and the second set of front wheels and the chassis 141. The location of dampers 147 between the sets of front wheels and the chassis 141 enables the damping system 146 to absorb the vibration or oscillations (e.g., vertical oscillations) generated due to deaccelerating the C-arm gantry 110 to a stop during the rotational movement of the C-arm gantry 110 in a single or combined direction (e.g., in a circumferential direction 184 about rotational axis 182 (see FIG. 2) and/or in the orbital direction 174).

The damping system 146 also includes plates 148. For example, a first damper may be disposed between a first plate and a second plate. Also, a second damper may be disposed between a third plate and a fourth plate. The plates may be made of aluminum. The first damper and the second damper may each include one or more elastomeric (e.g., rubber) bodies. In certain embodiments, the first damper and the second damper may each include three smaller elastomeric bodies. In certain embodiments, the first damper and the second damper may each include a single larger elastomeric body. In certain embodiments, each damper 147 may include 1, 2, 3, or more elastomeric bodies. In certain embodiments, the damper may include two conic parts to have a higher stiffness in a lateral direction than in a vertical direction to help with motion control. The dampers 147 are specifically tuned (e.g., based on the number and material of the elastomeric bodies) to absorb the vibrations generated due to deaccelerating the C-arm gantry 110 to a stop during the rotational movement of the C-arm gantry 110 in a single or combined direction (e.g., in a circumferential direction 184 about rotational axis 182 and/or in the orbital direction 174 (see FIG. 2)).

The damping system 146 further includes interfaces 149 having ball joints. The interfaces 149 may be made of aluminum. The interfaces 149 couple the damping system 146 to the chassis 141. For example, a first interface may be disposed on a side of the first plate opposite the first damper. Also, a second interface may be disposed on a side of the third plate opposite the second damper. The first set of free wheels may be disposed on a side of the second plate opposite the first damper. The second set of free wheels may be disposed on a side of the fourth plate opposite the second damper. Each ball joint is configured to rotate independently of the set of free wheels its associated with. Each damper 147, its associated plates 148, and associated interface 149 form a damping unit. In addition, each ball joint is configured to enable the damping system 146 (each damping unit) to tilt laterally relative to a vertical axis (e.g. rotational axis of the ball joint). This provides an additional degree of freedom in movement of each damping unit. Each ball joint enables each associated damping unit to adapt to the floor flatness (i.e. to counter or compensate for a lack of flatness with the floor). Each damping unit may be located on respective ends of the two arms of the Y-arm distal from the central arm.

The mobile X-ray imaging system 100 further includes a controller 150 including a processor 152 and a non-transitory memory 154. A method for controlling the mobile X-ray imaging system 100 may be stored as executable instructions 155 in the non-transitory memory 154 and executed by the processor 152.

The mobile X-ray imaging system 100 further include a user interface 160 for receiving input from a user or operator of the mobile X-ray imaging system 100. The user interface 160 may be communicatively coupled to the controller 150 for providing commands input by a user via the user interface 160 to the controller 150. The user interface 160 may include one or more of a keyboard, a mouse, a trackball, one or more knobs, one or more joysticks, a touchpad, a touchscreen, one or more hard and/or soft buttons, a smartphone, a microphone, a virtual reality apparatus, and so on. The user interface 160 may thus enable voice control, and display of information such as an interactive display device (e.g., touchscreen). In some examples the user interface 160 may be remotely located relative to the mobile X-ray imaging system 100. For example, the user interface 160 may be communicatively coupled to the controller 150 and/or the mobile X-ray imaging system 100 via a wired or wireless connection, and may be positioned away from the mobile base 140.

As an example, the memory 154 may store processor-executable software code or instructions (e.g., firmware or software), which are tangibly stored on a non-transitory computer readable medium. Additionally or alternatively, the memory 154 may store data. As an example, the memory 154 may include a volatile memory, such as random access memory (RAM), and/or a nonvolatile memory, such as read-only memory (ROM), flash memory, a hard drive, or any other suitable optical, magnetic, or solid-state storage medium, or a combination thereof. Furthermore, the processor 152 may include multiple microprocessors, one or more "general-purpose" microprocessors, one or more special-purpose microprocessors, and/or one or more application specific integrated circuits (ASICS), or some combination thereof. For example, the processor 152 may include one or more reduced instruction set (RISC) or complex instruction set (CISC) processors. The processor 152 may include multiple processors, and/or the memory 154 may include multiple memory devices.

A user of the mobile X-ray imaging system 100 may input a desired isocenter position via the user interface 160, for example. The controller 150 may then determine position adjustments to one or more of the C-arm gantry 110 and the mobile base 140 to align an isocenter of the mobile X-ray imaging system 100 with the desired isocenter position. As another example, a user of the mobile X-ray imaging system 100 may directly control the position of one or more components of the mobile X-ray imaging system 100 relative to other components of the mobile X-ray imaging system 100 via the user interface 160. For example, the user may directly input, via a joystick or knob, for example, position adjustments to one or more components of the mobile X-ray imaging system 100. As another example, the motion of the components of the mobile X-ray imaging system 100 may be pre-programmed such that the user does not directly control any movement, but instead initiates the start of the pre-programmed motion. The motion may include complex motions, with continuous motion of the isocenter.

The controller 150 is further communicatively coupled to a display device 165 for displaying one or more X-ray images acquired via the X-ray detector 107. Further, in some examples, one or more of the controller 150, the user interface 160, and the display device 165 may be positioned away from (e.g., remotely from) the remaining components of the mobile X-ray imaging system 100.

The mobile X-ray imaging system 100 may further include a cooling system 168 for cooling the X-ray source 105 and/or the X-ray detector 107. The cooling system 168 may include one or more flexible tubes and a pump, as an illustrative and non-limiting example, for providing cooling fluid to the X-ray source 105 to transfer thermal energy away from the X-ray source 105. The cooling system 168 may actively cool the X-ray source 105 and the X-ray detector 107 independently, or in some examples may cool the X-ray detector 107 by any suitable type of derivation of the cooling circuit for the X-ray source 105.

Figures 2, 3:
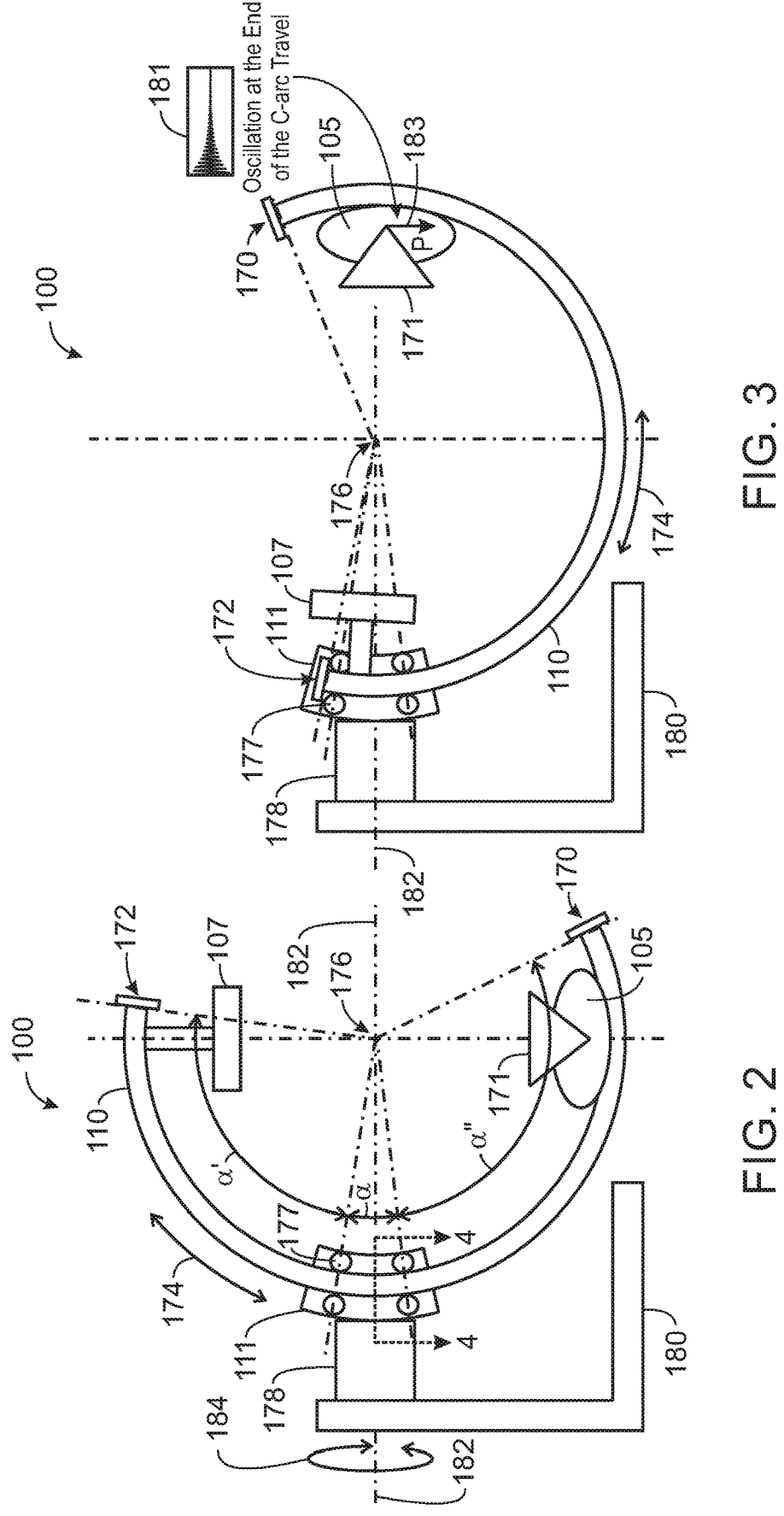
FIG. 2 is a schematic diagram of a side view of a portion of a mobile X-ray imaging system and its associated movements, in accordance with aspects of the present disclosure.
FIG. 3 is a schematic diagram of a side view of the portion of the mobile X-ray imaging system in FIG. 2 after the deacceleration phase of the C-arc motion, in accordance with aspects of the present disclosure.

FIG. 2 is a schematic diagram of a side view of a portion of the mobile X-ray imaging system 100 and its associated movements. The mobile X-ray imaging system 100 includes the C-arm gantry 110. The C-arm gantry 110 is made of carbon fiber. The mobile X-ray system 100 also includes the X-ray radiation source 105 coupled to a first end 170 of the C-arm gantry 110 and the X-ray detector 107 coupled to a second end 172 of the C-arm gantry 110 opposite the first end 170. A collimator 171 is coupled to the X-ray radiation source 105 and is configure to collimate the X-ray beam.

Figures 4, 5:
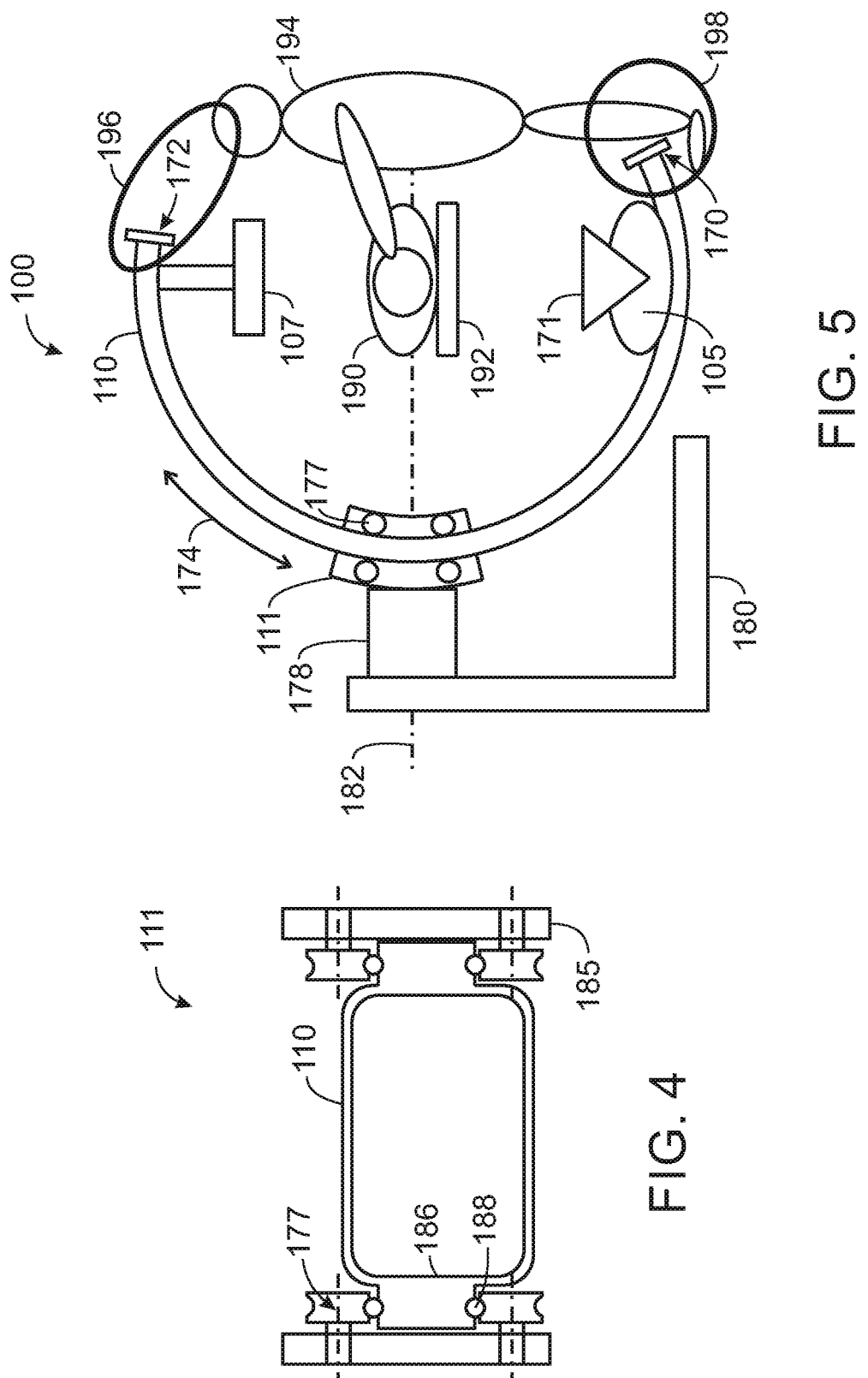
FIG. 4 is a schematic diagram of a cross-section of a C-arm carrier of the mobile X-ray imaging system in FIG. 2, taken along line 4-4 in FIG. 2, in accordance with aspects of the present disclosure.
FIG. 5 is a schematic diagram of a technologist interacting with a patient and the mobile X-ray imaging system in FIG. 2, in accordance with aspects of the present disclosure.

The C-arm gantry 110 is coupled to the C-arm carrier 111 (e.g., C-arm rotation device) is configure to rotate the C-arm gantry 110 in an orbital direction 174 relative to the C-arm carrier 111 about an isocenter 176 (of the X-ray radiation source 105 and the X-ray detector 107). The C-arm carrier 111 includes rollers 177 (e.g., guiding rollers) to guide movement of the C-arm gantry 110 relative to the C-arm carrier 111. The structure of the C-arm carrier 111 is shown in FIG. 4.

The C-arm carrier 111 is coupled to a pivot 178 (e.g., pivot point or shaft). The pivot 178 is coupled to a structure 180. The pivot 178 (in conjunction with a motorized system) is configured to rotate both the C-arm carrier 111 and the C-arm gantry 110 about a rotational axis 182 (e.g., horizontal axis) of the pivot 178 as indicated by arrow 184. In certain embodiments, the structure 180 is a mobile base (e.g., mobile base 140 in FIG. 1). In certain embodiments, the structure 180 is an L-arm coupled to the mobile base. In certain embodiments, the L-arm may rotate about an end of the L-arm coupled to the mobile base.

To obtain a good quality image when performing an orbital CBCT, the travel of the C-arm gantry 110 ($\alpha'+\alpha''$) should be approximately 200 degrees. In contrary, a total range of travel ($\alpha+\alpha'+\alpha''$) of the C-arm gantry 110 needs to be limited (e.g., as illustrated in FIG. 5) to provide sufficient access to the patient (e.g., for the technologist) and sufficient visibility of the screen or display (e.g., for the technologist) which is normally located behind the C-arm gantry 110. In this case, the angle $\alpha$ needs to as small as possible. Since the C-arm gantry 110 is made of carbon fiber the effort by the guiding rollers 177 of the C-arm carrier 111 is limited which helps reduce the angle $\alpha$.

However, carbon fiber is known to have a very low damping rate (e.g., compared to aluminum) which results in an undesired effect that could affect image quality. FIG. 3 is a schematic diagram of a side view of the portion of the mobile X-ray imaging system 100 in FIG. 2 after the deacceleration phase of the C-arc motion. The mobile X-ray imaging system 100 is as described in FIG. 2. As depicted in FIG. 3, the C-arm gantry 110 has been moved or rotated in the orbital direction 174 until the C-arm gantry 110 deaccelerated and reached the end of the C-arm motion or travel path. Due to the C-arm gantry 110 being made of carbon fiber (and having a very low damping rate), the deacceleration and stopping of the C-arm motion in the orbital direction 174 results in a lot of vibrations (e.g., oscillations as indicated by reference numeral 181) for several seconds due to force 183 generated by the X-ray radiation source 105 (e.g., weighing approximately 60 kilograms) being far from the C-arm carrier 111 when the C-arm motion is stopped. The vibrations may also occur before the end of the C-arm motion. Vibrations can also occur when the C-arm is not fully expended and the pivot 178 is angulated (i.e., rotation about the pivot 178). Without a damping system, these vibrations would affect image quality (e.g., create blurriness).

FIG. 4 is a schematic diagram of a cross-section of the C-arm carrier 111 of the mobile X-ray imaging system 100 in FIG. 2, taken along line 4-4 of FIG. 2. As depicted in FIG. 4, a portion of the C-arm gantry 110 is disposed within the C-arm carrier 111. In particular, portion of the C-arm gantry 110 is flanked by walls 185 of the C-arm carrier 111. The C-arm gantry 110 has tracks 186 on opposite sides of the C-arm gantry 110. Rods 188 are disposed along the tracks 186. Guiding rollers 177 (e.g., bearings) are coupled to each wall 185 and interface with respective rods 188 to move along the tracks 186 to move the C-arm gantry 110. As mentioned above, having the C-arm gantry 110 made of carbon fiber limits the effort by the guiding rollers 177 of the C-arm carrier 111 enabling the reduction of the angle $\alpha$ shown in FIG. 2.

FIG. 5 is a schematic diagram of a technologist interacting with a patient and the mobile X-ray imaging system 100 in FIG. 2. The mobile X-ray imaging system 100 is as described in FIG. 2. As depicted in FIG. 5, a patient 190 (e.g., subject) is disposed on a table 192 for imaging with the mobile X-ray imaging system 100. As depicted in FIG. 5, a technologist 194 is helping the position the patient 190. The head of the technologist 194 in certain instances may interfere with the end 172 of the C-arm gantry 110 as indicated by reference numeral 196 during C-arm motion in the orbital direction 174. Also, the legs of the technologist 194 in certain circumstances may interfere with the end 170 of the C-arm gantry 122 as indicated by reference numeral 198 during C-arm motion in the orbital direction 174. For these reasons, as noted above, the total range of travel of the C-arm gantry 110 ($\alpha+\alpha'+\alpha''$) where angle $\alpha$ is as small as possible.

Figure 6:
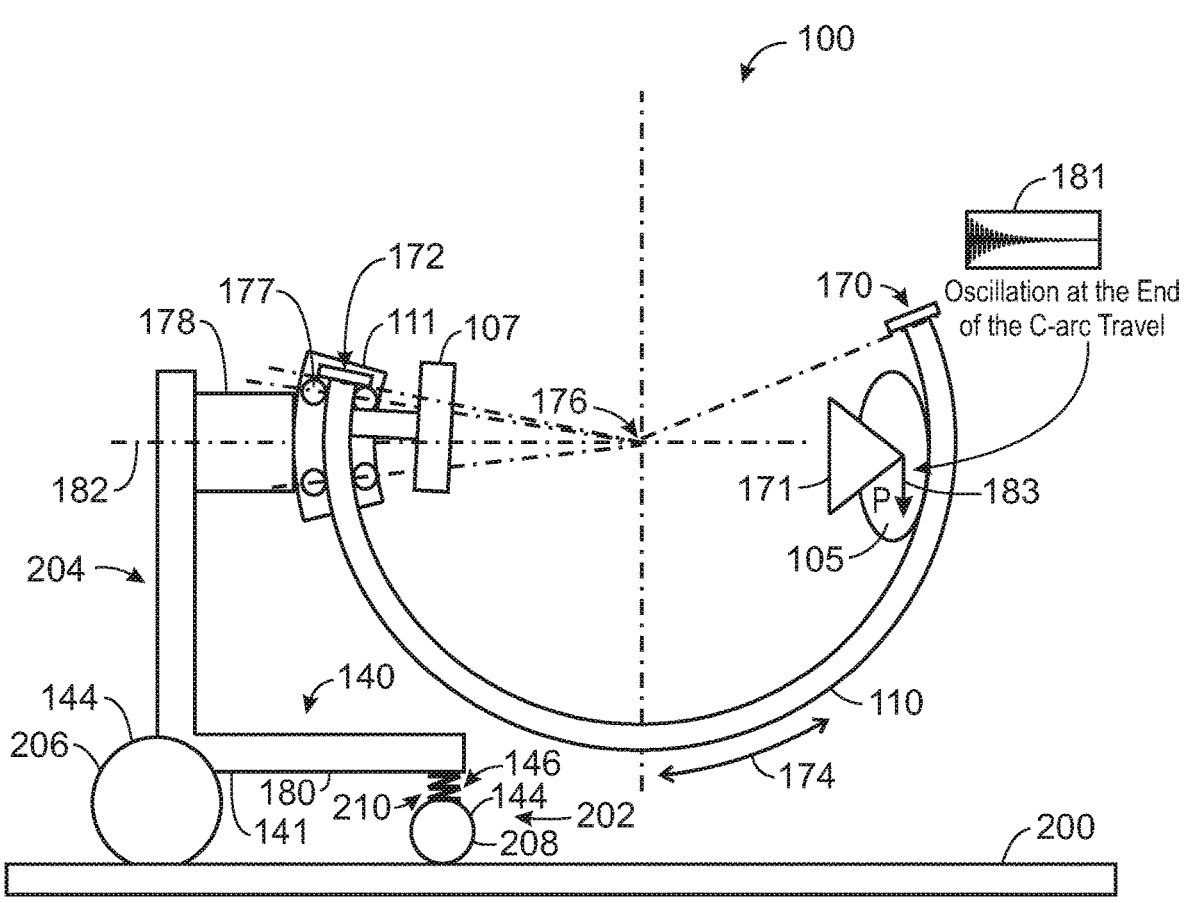
FIG. 6 is a schematic diagram of a side view of the mobile X-ray imaging system of FIG. 2 having a mobile base and a damping system, in accordance with aspects of the present disclosure.

FIG. 6 is a schematic diagram of a side view of the mobile X-ray imaging system 100 of FIG. 2 having the mobile base 140 and the damping system 146. The mobile X-ray imaging system 100 is as described in FIG. 2. As depicted, the structure 180 is the mobile base 140. The C-arm carrier 111 is coupled to the mobile base 140 via the pivot 178. The mobile base 140 is configured to move (e.g., translocate) the mobile X-ray imaging system 100 from one location to another location on a floor 200. The mobile base 140 includes the chassis 141. In certain embodiments, the chassis 141 includes a Y-arm having a central arm and two arms angled relative to a longitudinal axis of the central arm forming a Y-shape. Distal ends of the two arms (i.e., the ends of the two arms located away from the split from the central arm) are located towards a front side 202 of the mobile X-ray imaging system 100 (i.e., on the side of the mobile x-ray imaging system 100 with the C-arm gantry 110). As depicted, the mobile base 140 includes wheels 144 located both at rear side 204 and at the front side 202 of the mobile X-ray imaging system 100. Although only a single wheel 144 is depicted at both the rear side 204 and at the front side 202, multiple wheels 144 and/or multiple sets of wheels 144 may be located at both the rear side 204 and at the front side 202 of the mobile base 140 of the mobile X-ray imaging system 100. For example, one or more drive wheels 206 or sets of drive wheels 206 may be located at the rear side 204 of the mobile base 140. One or more motors may be utilized for driving one or more drive wheels 206 or sets of drive wheels 206 to adjust a position of the mobile base 140 (and, thus, the mobile X-ray imaging system 100). Also, one or more un-motorized or free wheels 208 (e.g., front wheels) or sets of free wheels 208 (e.g., front wheels) may be located at the front side 202 of the mobile base 140. In addition, one or more of the wheels 144 may be free or un-motorized, as described further herein. For example, the free wheels 208 may include a first set of free wheels 208 (e.g., first set of front wheels) and a second set of free wheels 208 (e.g., second set of front wheels). The first set of free wheels 208 and the second set of free wheels 208 may be located on respective ends of the two arms of the Y-arm distal from central arm.

The mobile X-ray imaging system 100 further includes the damping system 146. The damping system 146 is configured to dampen vibrations that occur when the C-arm gantry 110 (e.g., made of carbon fiber) deaccelerates (e.g., during the deacceleration phase) to a stop during rotational movement of the C-arm gantry 110 in the orbital direction 174. In certain embodiments, the damping system 146 is configured to dampen vibrations (e.g., oscillations) at a frequency of approximately 3 Hz. The damping system 146 includes one or more damping units 210. Although only one damping unit 210 is illustrated, the damping system 146 may include multiple damping units 210. For example, respective damping units 210 may be disposed between the first set of front wheels 208 and the chassis 141 and the second set of front wheels 208 and the chassis 141 (see FIGS. 7 and 8). The location of the damping units 210 between the sets of front wheels and the chassis 141 enables the damping system 146 to absorb the vibration or oscillations (e.g., vertical oscillations) generated due to deaccelerating the C-arm gantry 110 to a stop during the rotational movement of the C-arm gantry 110 in a single or combined direction (e.g., in a circumferential direction 184 about rotational axis 182 and/or in the orbital direction 174 (see FIG. 2)).

Each damping unit 210 includes a damper. Each damping unit 210 also includes plates. For example, a first damper may be disposed between a first plate and a second plate. Also, a second damper may be disposed between a third plate and a fourth plate. The plates may be made of aluminum. The first damper and the second damper may each include one or more elastomeric (e.g., rubber) bodies. In certain embodiments, the first damper and the second damper may each include three smaller elastomeric bodies. In certain embodiments, the first damper and the second damper may each include a single larger elastomeric body. In certain embodiments, each damper may include 1, 2, 3, or more elastomeric bodies. The dampers are specifically tuned (e.g., based on the number and material of the elastomeric bodies) to absorb the vibrations generated due to deaccelerating the C-arm gantry 110 to a stop during the rotational movement of the C-arm gantry 110 in a single or combined direction (e.g., in a circumferential direction 184 about rotational axis 182 and/or in the orbital direction 174 (see FIG. 2)).

Each damping unit 210 further includes interfaces having ball joints. The interfaces couple the damping units 210 to the chassis 141. For example, a first interface may be disposed on a side of the first plate opposite the first damper. Also, a second interface may be disposed on a side of the third plate opposite the second damper. The first set of free wheels 208 may be disposed on a side of the second plate opposite the first damper. The second set of free wheels 208 may be disposed on a side of the fourth plate opposite the second damper. Each ball joint is configured to rotate independently of the set of free wheels 208 its associated with. Each damper, its associated plates, and associated interface (and ball joint) form a respective damping unit 210. In addition, each ball joint is configured to enable each damping unit 210 to tilt laterally relative to a vertical axis (e.g. rotational axis of the ball joint). This provides an additional degree of freedom in movement of each damping unit 210. Each ball joint enables each associated damping unit 210 to adapt to the floor 200. Each damping unit 210 may be located on respective ends of the two arms of the Y-arm distal from the central arm.

Figure 7:
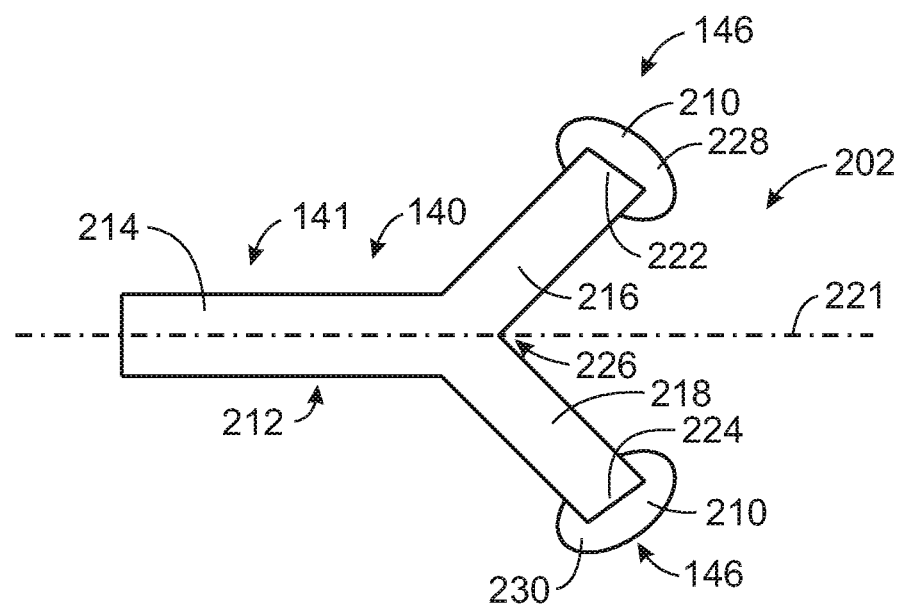
FIG. 7 is a schematic diagram of a top view of a chassis of a mobile base of the mobile X-ray imaging system in FIG. 6, in accordance with aspects of the present disclosure.

FIG. 7 is a schematic diagram of a top view of the chassis 141 of the mobile base of the mobile X-ray imaging system 100 in FIG. 6. As depicted in FIG. 7, the chassis 141 includes a Y-arm 212 having a central arm 214 and two arms 216, 218 angled (at greater than 0 degrees) relative to a longitudinal axis 221 of the central arm 214. The central arm 214 and the two arms 216, 218 form a Y-shape. Distal ends 222, 224 of the two arms 216, 218 (i.e., the ends 222, 224 of the two arms 216, 218 located away from the split (indicated by reference numeral 226 from the central arm 214) are located towards the front side 202 of the mobile X-ray imaging system 100 (i.e., on the side of the mobile x-ray imaging system 100 with the C-arm gantry 110, see FIG. 6).

As depicted in FIG. 7, the damping system 146 includes multiple damping units 210. In particular, the damping system 146 includes a first damping unit 228 located underneath the end 222 of the arm 216 of the Y-arm 212. The damping system 146 also includes a second damping unit 230 located underneath the end 224 of the arm 218 of the Y-arm 212. As described above, each damping unit 210 includes plates, a damper disposed between the plates, and an interface having a ball joint. The first damping unit 228 is disposed between the end 222 of the arm 216 of the Y-arm 212 and a first set of free wheels. The second damping unit 230 is disposed between the end 224 of the arm 218 of the Y-arm 212 and a second set of free wheels. The location of the damping units 210 between the sets of front wheels and the respective ends 222, 224 of the arms 216, 218 of the Y-arm 212 enables the damping system 146 to absorb the vibration or oscillations (e.g., vertical oscillations) generated due to deaccelerating the C-arm gantry to a stop during the rotational movement of the C-arm gantry in a single or combined direction (e.g., in a circumferential direction 184 about rotational axis 182 and/or in the orbital direction 174 (see FIG. 2)).

Figure 8:
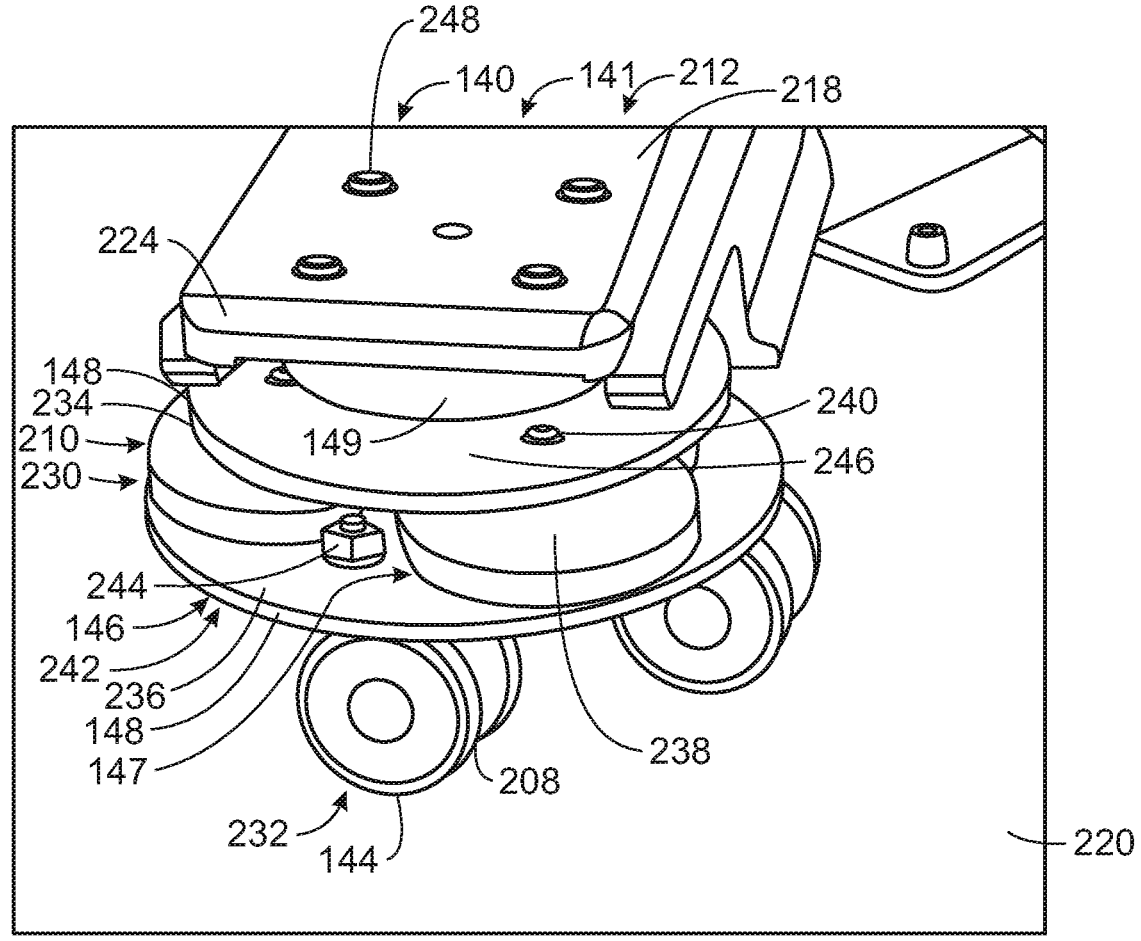
FIG. 8 is a perspective view of a damping unit coupled to a chassis of a mobile base of the mobile X-ray imaging system in FIG. 6, in accordance with aspects of the present disclosure.
Figure 10:
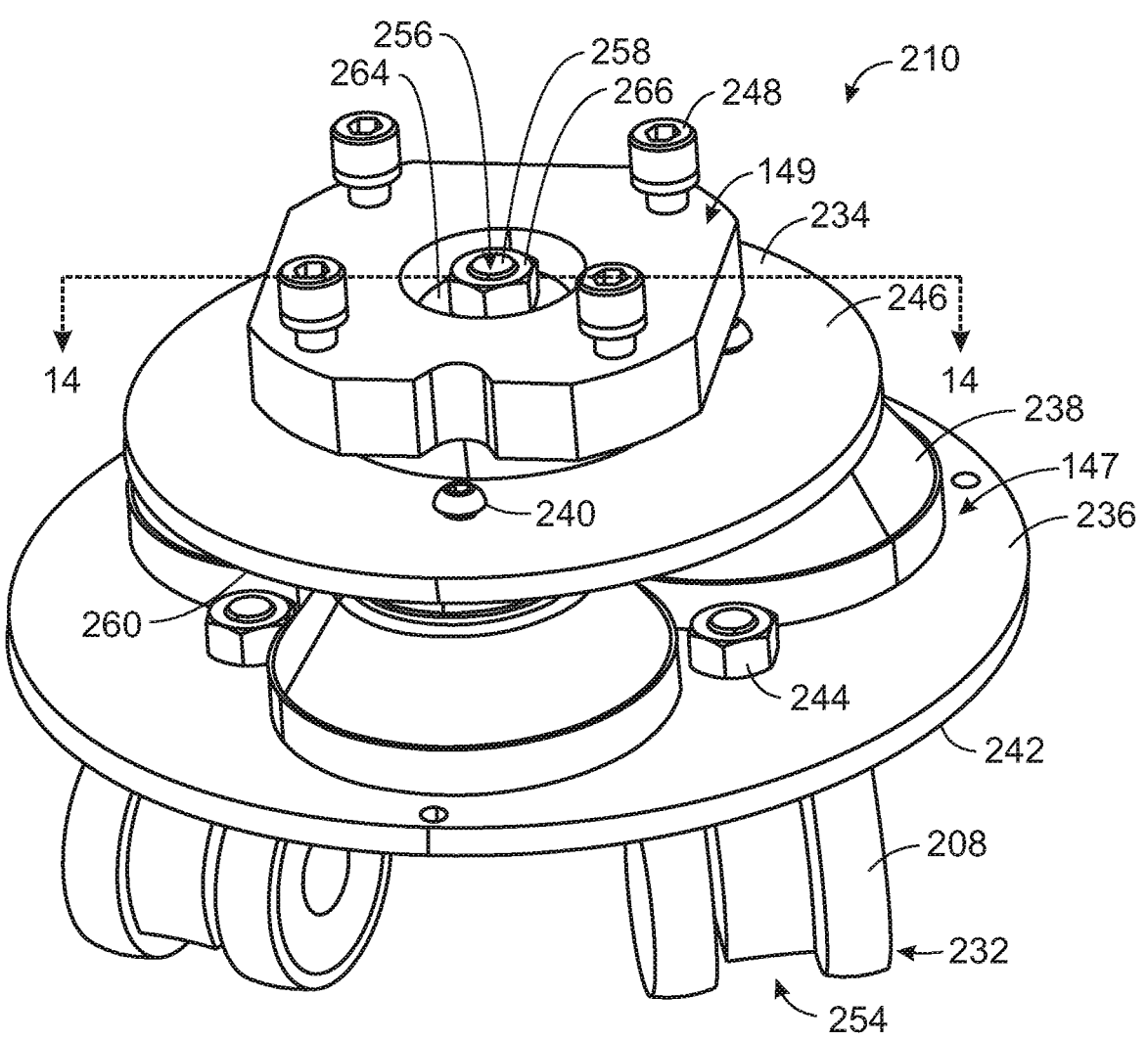
FIG. 10 is a perspective view of a damping unit, in accordance with aspects of the present disclosure.

FIG. 8 is a perspective view of the damping unit 210 coupled to the chassis 141 of the mobile base 140 of the mobile X-ray imaging system 100 in FIG. 6. In particular, the damping unit 230 coupled to the end 224 of the arm 218 of the Y-arm 212 in FIG. 7 is depicted. The description of the damping unit 230 applies to the damping unit 228 in FIG. 7. As depicted in FIG. 8, the damping unit 210 is located underneath the end 224 of the arm 218 of the Y-arm 212. In particular, the damping unit 210 is located (e.g., vertically) between the end 224 of the arm 218 of the Y-arm 212 and a set 232 of free wheels 208 (e.g., set of front wheels). The set 232 of free wheels 208 may include three wheels 208 (although only two wheels are visible in FIG. 8). The number of wheels 208 in the set 232 may vary. As mentioned above, location of the damping unit 230 (and the damping unit 228) enables the damping system 146 to absorb the vibration or oscillations (e.g., vertical oscillations) generated due to deaccelerating the C-arm gantry to a stop during the rotational movement of the C-arm gantry in a single or combined direction (e.g., in a circumferential direction 184 about rotational axis 182 and/or in the orbital direction 174 (see FIG. 2)).

As depicted in FIG. 8, the damping unit 230 includes a first plate 234 and a second plate 236. The plates 234, 236 may be made of aluminum. The damper 147 is disposed between the first plate 234 (e.g., top plate) and the second plate 236 (e.g., bottom plate). As depicted, the damper 147 includes three elastomeric (e.g., rubber) bodies 238 (although only two elastomeric bodies 238 are visible in FIG. 8). In certain embodiments, each elastomeric body 238 may increase in diameter in a direction from the first plate 234 to the second plate 236. In certain embodiments, the damper 147 may include a single larger elastomeric body 238. The damper 147 is specifically tuned (e.g., based on the number and material of the elastomeric bodies) to absorb the vibrations generated due to deaccelerating the C-arm gantry to a stop during the rotational movement of the C-arm gantry in a single or combined direction (e.g., in a circumferential direction 184 about rotational axis 182 and/or in the orbital direction 174 (see FIG. 2)).

Each elastomeric body 238 is coupled to the first plate 234 via a respective fastener 240 (e.g., nut and bolt) extending through a corresponding opening in the first plate 234. Each wheel 208 of the set 232 of free wheels 208 is coupled on a side 242 of the second plate 236 opposite the damper 147 via a respective fastener 244 (e.g., nut and bolt) extending through a corresponding opening in the second plate 236.

The damping unit 230 also includes the interface 149 having a ball joint. As depicted, the interface 149 is coupled to a side 246 of the first plate 234 opposite the damper 147. The interface 149 is coupled to the end 224 of the arm 218 of the Y-arm 212 via a plurality of fasteners 248 extending through openings in the end 224 of the arm 218. The ball joint couples the interface 149 the first plate 234. The ball joint is configured to rotate independently of the set 232 of free wheels 208. In addition, the ball joint is configured to enable the damping unit 230 to tilt laterally relative to a vertical axis (e.g. rotational axis of the ball joint). This provides an additional degree of freedom in movement of the damping unit 230. Each ball joint enables the damping unit 230 to adapt to the floor 220.

Figure 9:
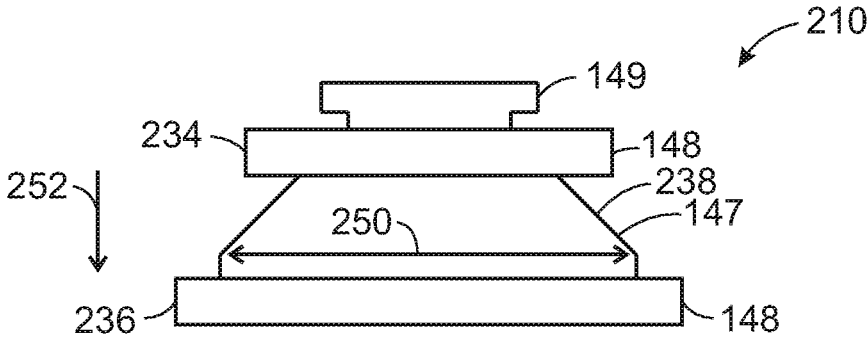
FIG. 9 is a schematic view of a side of a damping unit (e.g., having a damper with a single elastomeric body), in accordance with aspects of the present disclosure.

FIG. 9 is a schematic view of a side of the damping unit 210 (e.g., having the damper 147 with a single elastomeric body 238). As depicted, the single elastomeric body 238 (having a greater area than each of the three elastomeric bodies 238 in FIG. 8) is disposed between the first plate 234 and the second plate 236. The interface 149 is coupled to the first plate 234. As depicted, a diameter 250 of the single elastomeric body 238 increases in a direction 252 from the first plate 234 to the second plate 236. The single elastomeric body 238 functions similar to three elastomeric bodies 238 in FIG. 8.

Figure 11:
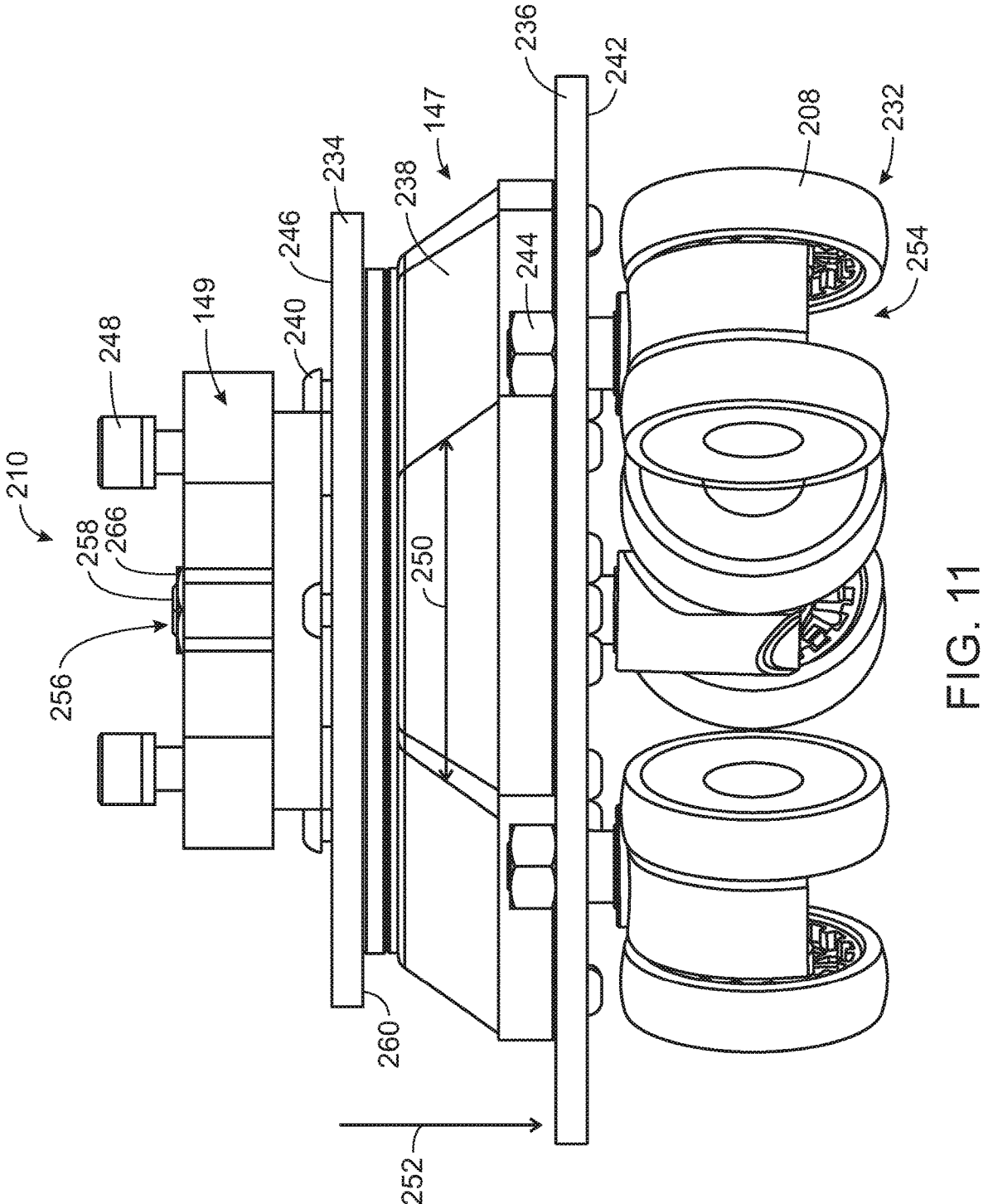
FIG. 11 is a side view of the damping unit in FIG. 10, in accordance with aspects of the present disclosure.
Figure 12:
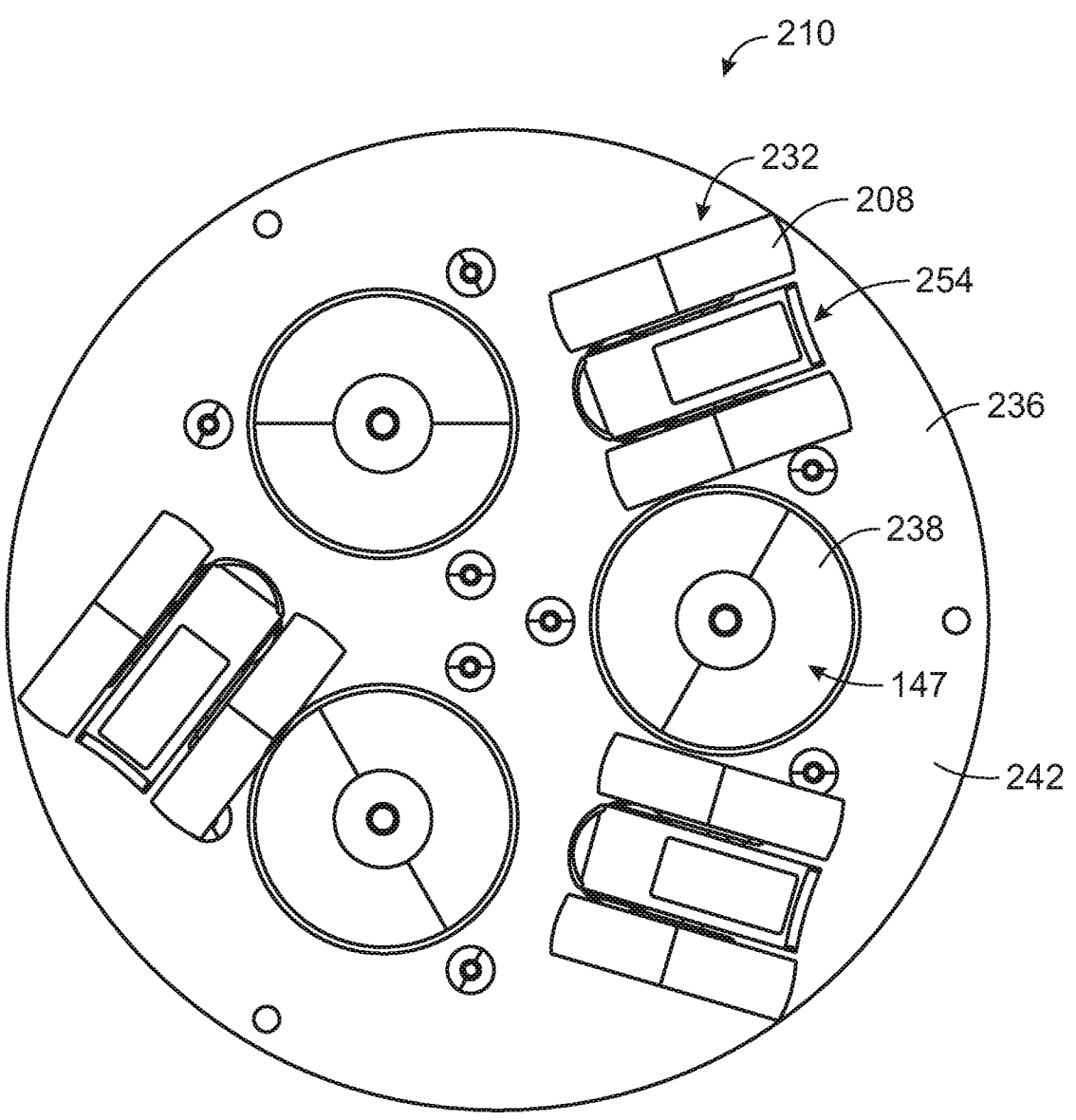
FIG. 12 is a bottom view of the damping unit in FIG. 10, in accordance with aspects of the present disclosure.
Figure 13:
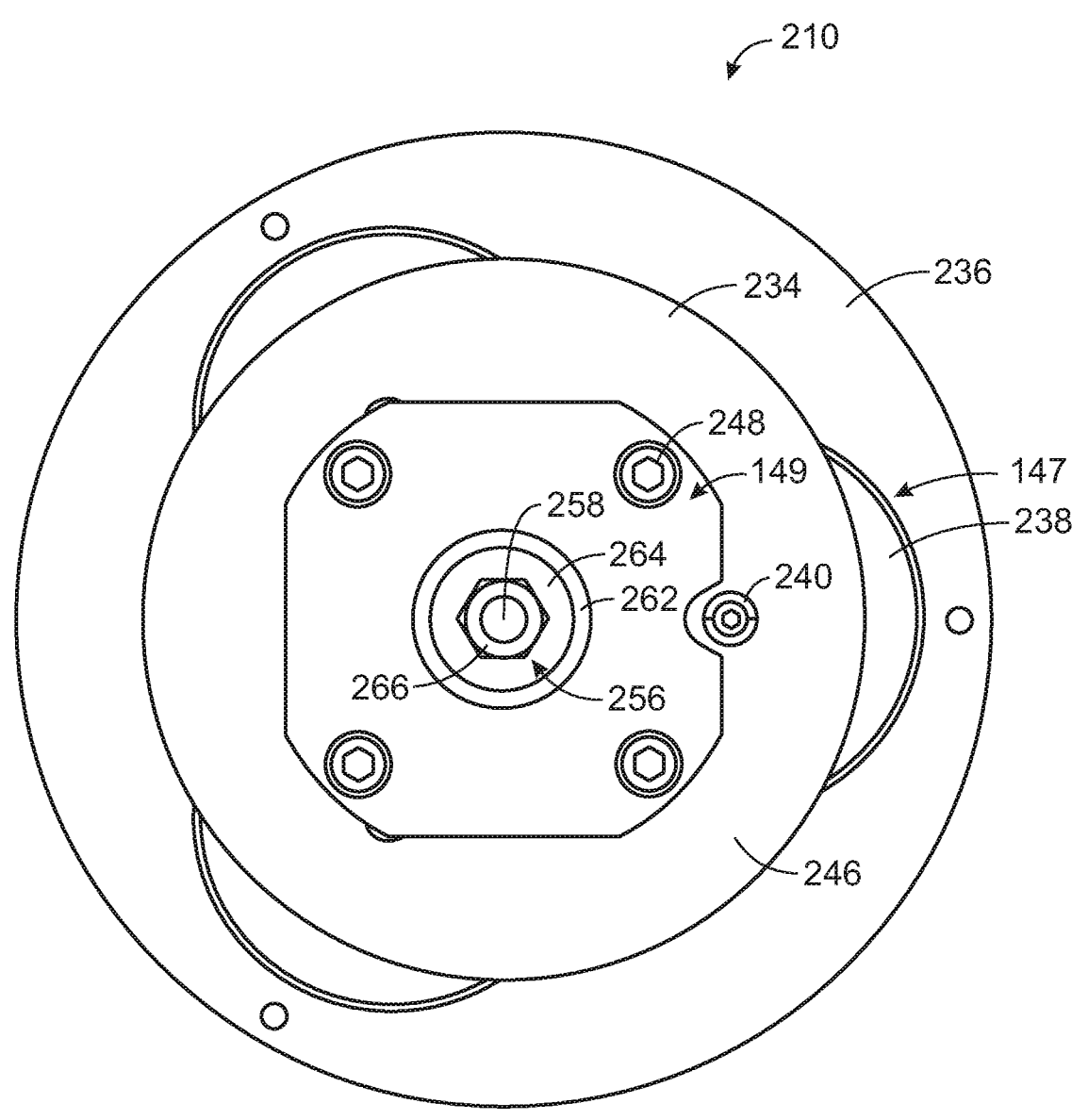
FIG. 13 is a top view of the damping unit in FIG. 10, in accordance with aspects of the present disclosure.
Figure 14:
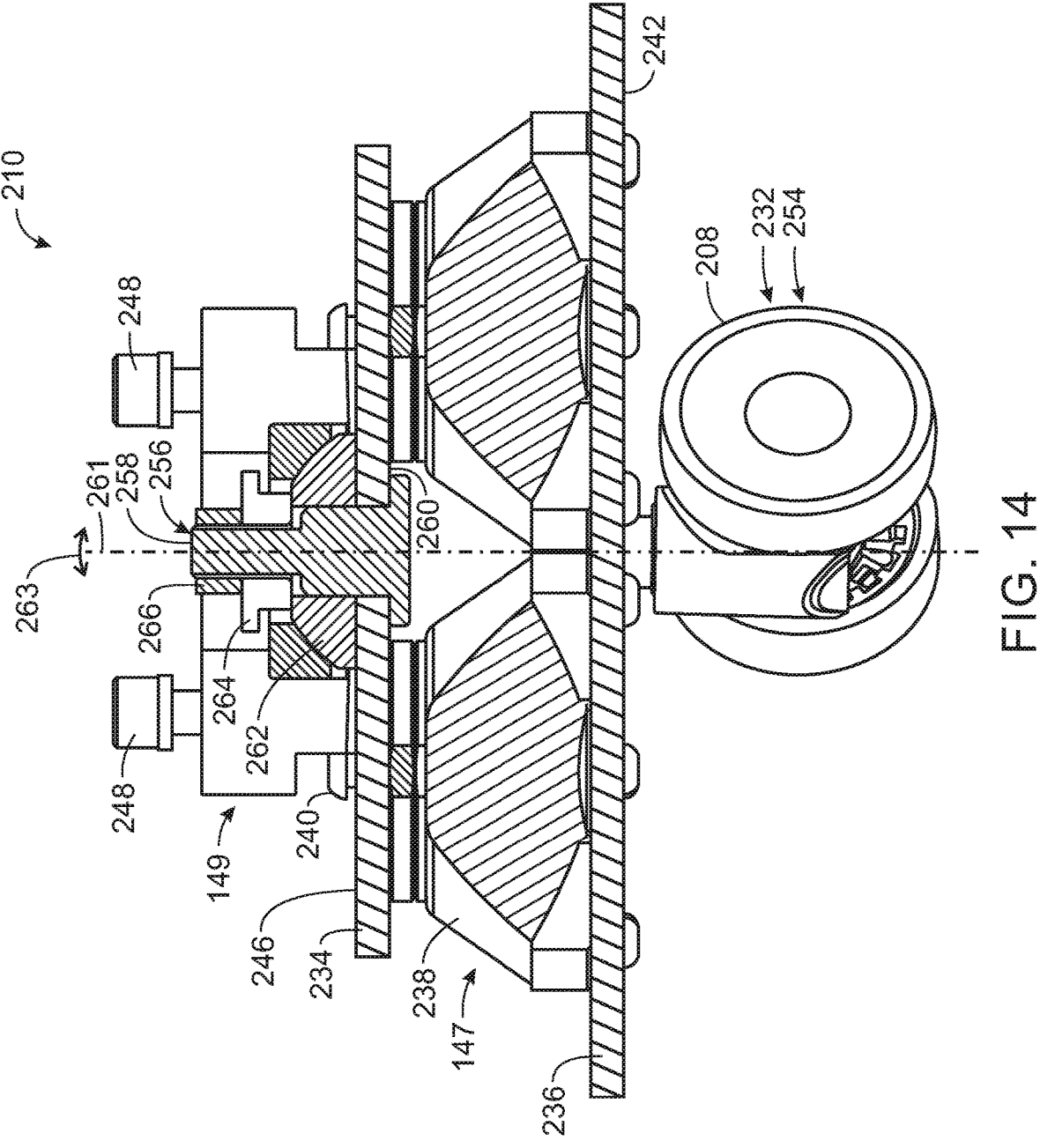
FIG. 14 is a cross-sectional view of the damping unit in FIG. 10, taken along line 14-14 in FIG. 10, in accordance with aspects of the present disclosure.

FIGS. 10-14 are different views of the damping unit 210. As depicted in FIGS. 10-14, the damping unit 210 is coupled to the set 232 of free wheels 208 (e.g., multiple pairs 254 of free wheels 208). The damping unit 210 includes the first plate 234 and the second plate 236. The plates 234, 236 may be made of aluminum. The damper 147 is disposed between the first plate 234 (e.g., top plate) and the second plate 236 (e.g., bottom plate). As depicted, the damper 147 includes three elastomeric (e.g., rubber) bodies 238. In certain embodiments, each elastomeric body 238 may increase in diameter 250 in the direction 252 from the first plate 234 to the second plate 236 (as depicted in FIG. 11). In certain embodiments, the damper 147 may include a single larger elastomeric body 238 as depicted in FIG. 9. The damper 147 is specifically tuned (e.g., based on the number and material of the elastomeric bodies) to absorb the vibrations generated due to deaccelerating the C-arm gantry to a stop during the rotational movement of the C-arm gantry in a single or combined direction (e.g., in a circumferential direction 184 about rotational axis 182 and/or in the orbital direction 174 (see FIG. 2)).

Each elastomeric body 238 is coupled to the first plate 234 via a respective fastener 240 (e.g., nut and bolt) extending through a corresponding opening in the first plate 234. Each pair 254 of wheels 208 of the set 232 of free wheels 208 is coupled on a side 242 of the second plate 236 opposite the damper 147 via a respective fastener 244 (e.g., nut and bolt) extending through a corresponding opening in the second plate 236.

The damping unit 210 also includes the interface 149 having a ball joint 256. As depicted, the interface 149 is coupled to the side 246 of the first plate 234 opposite the damper 147. The interface 149 is coupled to the end of the arm of the Y-arm via a plurality of fasteners 248 extending through openings in the end of the arm. The ball joint 256 couples the interface 149 the first plate 234. The ball joint 256 is configured to rotate independently of the set 232 of free wheels 208. In addition, the ball joint 256 is configured to enable the damping unit 210 to tilt laterally relative to a vertical axis 261 (e.g. rotational axis of the ball joint 256) (see FIG. 14) as indicated by arrow 263. This provides an additional degree of freedom in movement of the damping unit 210. The ball joint 256 enables the damping unit 210 to adapt to the floor. The ball joint 256 includes a stud 258 extending from a side 260 to the side 246 of the first plate 234. On the side 246 of the first plate 234, the stud 258 extends through a socket 262 and a washer 264 and is secured to the first plate 234 via a fastener 266 (e.g., nut).

Technical effects of the disclosed embodiments include providing a damping system located (e.g., vertically located) between the Y-arm of the chassis and the front wheels coupled to the Y-arm that enables the absorption of oscillations (e.g., vertical oscillations) or vibrations during the deceleration phase of C-arm motion as it approaches a stop. In particular, the damping system enables the utilization of a C-arm made of carbon fiber (which has a very low damping coefficient relative to aluminum) as part of an interventional C-arm medical imaging system that is configured to perform CBCT at a fast speed and decelerate with similar timing compared to a C-arm medical imaging system made having a C-arm made aluminum. The damping of the vibrations when the C-arm deaccelerates to a stop during movement of the C-arm in a single or combined direction enables quality images (e.g., lacking blurriness).

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A mobile X-ray imaging system, comprising:
an X-ray radiation source;
an X-ray detector;
a C-arm having the X-ray radiation source disposed on a first end and the X-ray detector disposed on a second end opposite the first end;
a C-arm rotation device coupled to the C-arm and configured to rotate the C-arm in an orbital direction relative to the C-arm rotation device; and
a mobile base coupled to the C-arm rotation device via a pivot point configured to rotate both the C-arm rotation device and the C-arm relative to the mobile base, wherein the mobile base is configured to move the mobile X-ray imaging system, and wherein the mobile base comprises a damping system configured to dampen vibrations that occur when the C-arm deaccelerates to a stop during rotational movement of the C-arm in a single or combined direction, wherein the mobile base comprises a chassis and at least one set of wheels coupled to the chassis, and the damping system comprises a damper disposed between the at least one set of wheels and the chassis, and wherein the chassis comprises a Y-arm having a central arm and two arms angled relative to a longitudinal axis of the central arm, wherein the mobile base comprises both a first set of wheels and a second set of wheels coupled to the chassis at respective ends of the two arms distal from the central arm, and the damping system comprises both a first damper disposed between the first set of wheels and the chassis and a second damper disposed between the second set of wheels and the chassis.

2. The mobile X-ray imaging system of claim 1, wherein the damper comprises at least one elastomeric body.

3. The mobile X-ray imaging system of claim 1, wherein the C-arm is made of carbon fiber.

4. The mobile X-ray imaging system of claim 1, wherein the damping system is configured to dampen vibrations at a frequency of approximately 3 hertz.

5. The mobile X-ray imaging system of claim 2, wherein the damper comprises more than one elastomeric body.

6. The mobile X-ray imaging system of claim 2, wherein the damping system comprises a first plate, a second plate, and the at least one elastomeric body disposed between the first plate and the second plate.

7. The mobile X-ray imaging system of claim 6, wherein the damping system comprises an interface having a ball joint coupled to the first plate on a first side of the first plate opposite the at least one elastomeric body, the interface couples the damping system to the chassis, the ball joint is configured to rotate independently of the at least one set of wheels, and the ball joint is configured to enable the damping system to tilt laterally relative to a vertical axis to counter a lack of flatness of a surface that the mobile X-ray imaging system is disposed on.

8. The mobile X-ray imaging system of claim 7, wherein the at least one set of wheels is coupled to a second side of the second plate opposite the at least one elastomeric body.

9. A damping system for a mobile X-ray imaging system, comprising:
a first plate;
a second plate; and
a first damper comprising at least one elastomeric body disposed between the first plate and the second plate, wherein the mobile X-ray imaging system comprises a C-arm made of carbon fiber and having an X-ray radiation source disposed on a first end and an X-ray detector disposed on a second end opposite the first end, a C-arm rotation device coupled to the C-arm and configured to rotate the C-arm in an orbital direction relative to the C-arm rotation device, and a mobile base coupled to the C-arm rotation device via a pivot point configured to rotate both the C-arm rotation device and the C-arm relative to the mobile base, wherein the mobile base is configured to move the mobile X-ray imaging system, and wherein the damping system is configured to dampen vibrations that occur when the C-arm deaccelerates to a stop during rotational movement of the C-arm in a single or combined direction, wherein the first damper comprises three elastomeric bodies, and wherein the damping system further comprises a third plate, a fourth plate, and a second damper comprising an additional three elastomeric bodies disposed between the third plate and the fourth plate.

10. The damping system of claim 9, wherein the second plate is configured to couple to a first set of wheels and the fourth plate is configured to couple to a second set of wheels.

11. The damping system of claim 9, wherein the damping system is configured to dampen vibrations at a frequency of approximately 3 hertz.

12. The damping system of claim 10, wherein the damping system further comprises a first interface having a first ball joint coupled to the first plate on a first side of the first plate opposite the three elastomeric bodies, a second interface having a second ball joint coupled to the third plate on a second side of the third plate opposite the additional three elastomeric bodies, wherein the first interface and the second interface are both configured to couple the damping system to a chassis of the mobile base.

13. The damping system of claim 12, wherein the first ball joint is configured to rotate independently of the first set of wheels, the second ball joint is configured to rotate independently of the second set of wheels, the first ball joint is configured to enable the first plate, the second plate, and the three elastomeric bodies to tilt laterally relative to a vertical axis to counter a lack of flatness of a surface that the mobile X-ray imaging system is disposed on, and the second ball joint is configured to enable the third plate, the fourth plate, and the additional three elastomeric bodies to tilt laterally relative to the vertical axis to counter the lack of flatness of the surface that the mobile X-ray imaging system is disposed on.

14. The damping system of claim 12, wherein the second plate is configured to couple to the first set of wheels on a third side of the second plate opposite the three elastomeric bodies, and the fourth plate is configured to couple the second set of wheels on a fourth side of the fourth plate opposite the additional three elastomeric bodies.

15. The damping system of claim 14, wherein the chassis comprises a Y-arm having a central arm and two arms angled relative to a longitudinal axis of the central arm, wherein the first interface, the first plate, the second plate, and the three elastomeric bodies are all configured to couple at a first end of a first arm of the two arms distal from the central arm, and wherein the second interface, the third plate, the fourth plate, and the additional three elastomeric bodies are all configured to couple at a second end of a second arm of the two arms distal from the central arm.

16. A mobile base for an X-ray imaging system, comprising:

a chassis comprising a Y-arm, wherein the Y-arm comprises a central arm and two arm angled relative to a longitudinal axis of the central arm;

a first set of wheels;

a second set of wheels, wherein the first set of wheels and the second set of wheels are coupled to respective ends of the two arms distal from the central arm; and a damping system comprising a first set of elastomeric bodies disposed between the first set of wheels and the Y-arm, and a second set of elastomeric bodies disposed between the second set of wheels and the Y-arm, wherein the X-ray imaging system comprises a C-arm made of carbon fiber and having an X-ray radiation source disposed on a first end and an X-ray detector disposed on a second end opposite the first end, a C-arm rotation device coupled to the C-arm and configured to rotate the C-arm in an orbital direction relative to the C-arm rotation device, and the C-arm rotation device is coupled to the mobile base via a pivot point configured to rotate both the C-arm rotation device and the C-arm relative to the mobile base, and wherein the mobile base is configured to move the X-ray imaging system, and the damping system is configured to dampen vibrations that occur when the C-arm deaccelerates to a stop during rotational movement of the C-arm in a single or combined direction.

* * * * *